(12) United States Patent
Gunaratnam et al.

(10) Patent No.: US 7,600,513 B2
(45) Date of Patent: *Oct. 13, 2009

(54) MASK AND HEADGEAR CONNECTOR

(75) Inventors: Michael K. Gunaratnam, Marsfield (AU); Philip R. Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 822 days.

This patent is subject to a terminal disclaimer.

(21) Appl. No.: 10/090,173

(22) Filed: Mar. 6, 2002

(65) Prior Publication Data

US 2002/0096176 A1    Jul. 25, 2002

Related U.S. Application Data

(63) Continuation of application No. 09/504,220, filed on Feb. 15, 2000, now Pat. No. 6,374,826, which is a continuation-in-part of application No. 29/115,618, filed on Dec. 16, 1999, now Pat. No. Des. 443,355.

(30) Foreign Application Priority Data

Jun. 18, 1999    (AU) ...................................... 1916/99
Jun. 18, 1999    (AU) ...................................... PQ1040

(51) Int. Cl.
*A62B 18/02*    (2006.01)
*A62B 18/08*    (2006.01)
*A44B 11/25*    (2006.01)

(52) U.S. Cl. ............................ 128/206.27; 128/205.25; 128/206.21; 24/615

(58) Field of Classification Search ............ 128/206.16, 128/205.25, 206.12, 206.24, 206.27, 206.28, 128/207.11, 206.21, 857, 863, 200.24, 201.22, 128/201.23, 201.24, 201.25, 201.26, 202.11, 128/203.29, 204.11, 204.29, 206.13, 206.18, 128/207.13; 24/30.55, 30.51, 336, 572.1, 24/573.1, 581.1, 578.1, 614–616; 36/50.1, 36/50.5
See application file for complete search history.

(56) References Cited

U.S. PATENT DOCUMENTS

| 2,097,676 A | 11/1937 | Shindel et al. | ......... 128/207.11 |
| 2,292,568 A | 8/1942 | Kanter et al. | .......... 128/203.28 |
| 2,823,671 A | 2/1958 | Garelick | ...................... 128/146 |
| 2,928,387 A | 3/1960 | Layne | ........................ 128/141 |
| 4,437,462 A | 3/1984 | Piljay et al. | ............ 128/201.11 |

(Continued)

FOREIGN PATENT DOCUMENTS

AU    A-59430/94    10/1995

(Continued)

OTHER PUBLICATIONS

European Search Report filed in EP 05026584.2 (Jan. 27, 2006.

*Primary Examiner*—Justine R Yu
*Assistant Examiner*—Annette F Dixon
(74) *Attorney, Agent, or Firm*—Nixon & Vanderhye P.C.

(57) ABSTRACT

A connector arrangement joining a respiratory mask and headgear is adapted for single-handed disengagement by the patient. A first, rigid connector part 470 is formed into the rigid mask frame 400, with a mating second connector 600 attached to a strap of the headgear. The connectors are held away from the patient's face by the connection to the mask frame.

42 Claims, 9 Drawing Sheets

U.S. PATENT DOCUMENTS

| | | | | |
|---|---|---|---|---|
| 4,802,262 | A * | 2/1989 | Kasai | 24/606 |
| 4,928,364 | A * | 5/1990 | Ikeda | 24/614 |
| 5,069,205 | A * | 12/1991 | Urso | 128/201.24 |
| 5,205,832 | A * | 4/1993 | Tuman | 604/179 |
| 5,243,971 | A * | 9/1993 | Sullivan et al. | 128/205.25 |
| 5,245,993 | A | 9/1993 | McGrady et al. | 128/201.25 |
| 5,263,234 | A * | 11/1993 | Fudaki | 24/662 |
| 5,291,880 | A | 3/1994 | Almovist et al. | 128/201.22 |
| 5,396,881 | A * | 3/1995 | Klein | 601/23 |
| 5,555,569 | A * | 9/1996 | Lane | 2/424 |
| 5,657,493 | A * | 8/1997 | Ferrero et al. | 2/428 |
| 5,662,101 | A | 9/1997 | Ogden et al. | 128/205.25 |
| 5,884,624 | A | 3/1999 | Barnett et al. | 128/206.24 |
| 5,918,598 | A | 7/1999 | Belfer et al. | 128/206.25 |
| 5,921,239 | A | 7/1999 | McCall et al. | 128/205.25 |
| 5,924,420 | A | 7/1999 | Reischel et al. | 128/206.21 |
| 5,996,192 | A * | 12/1999 | Haines et al. | 24/625 |
| 6,192,886 | B1 * | 2/2001 | Rudolph | 128/207.13 |
| 6,199,219 | B1 | 3/2001 | Silken et al. | 2/424 |
| D443,355 | S | 6/2001 | Gunaratnam et al. | |
| 6,374,826 | B1 * | 4/2002 | Gunaratnam et al. | 128/206.27 |
| 2003/0106557 | A1 * | 6/2003 | Viljanen et al. | 128/206.21 |
| 2003/0178026 | A1 * | 9/2003 | Byram | 128/206.21 |
| 2004/0025883 | A1 * | 2/2004 | Eaton et al. | 128/206.27 |
| 2004/0045551 | A1 * | 3/2004 | Eaton et al. | 128/206.21 |
| 2004/0112384 | A1 * | 6/2004 | Lithgow et al. | 128/206.21 |
| 2005/0011521 | A1 * | 1/2005 | Sprinkle et al. | 128/206.21 |
| 2005/0022820 | A1 * | 2/2005 | Kwok et al. | 128/206.21 |
| 2005/0076912 | A1 * | 4/2005 | Eifler et al. | 128/206.24 |
| 2005/0126573 | A1 * | 6/2005 | Jaffre et al. | 128/207.12 |
| 2005/0172969 | A1 * | 8/2005 | Ging et al. | 128/206.24 |
| 2006/0076019 | A1 * | 4/2006 | Ho | 128/206.24 |
| 2006/0096598 | A1 * | 5/2006 | Ho et al. | 128/206.24 |
| 2006/0162729 | A1 * | 7/2006 | Ging et al. | 128/206.27 |
| 2006/0196509 | A1 * | 9/2006 | Drew et al. | 128/206.21 |

FOREIGN PATENT DOCUMENTS

| | | |
|---|---|---|
| EP | 0958841 A2 | 11/1999 |
| FR | 2727836 | 6/1996 |
| GB | 684788 | 12/1952 |
| GB | 704167 | 2/1954 |
| GB | 2293410 | 3/1996 |
| WO | WO 87/01950 | 4/1987 |
| WO | WO 97/20597 | 6/1997 |
| WO | WO 98/48878 | 11/1998 |

* cited by examiner

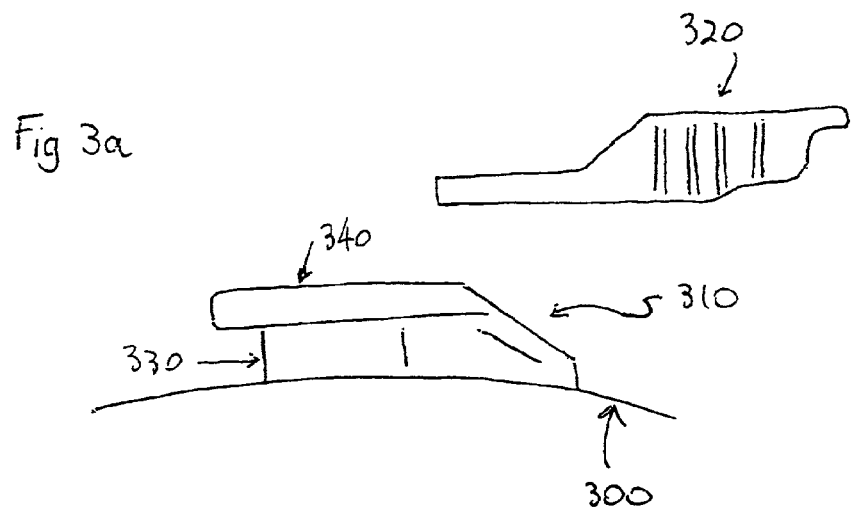
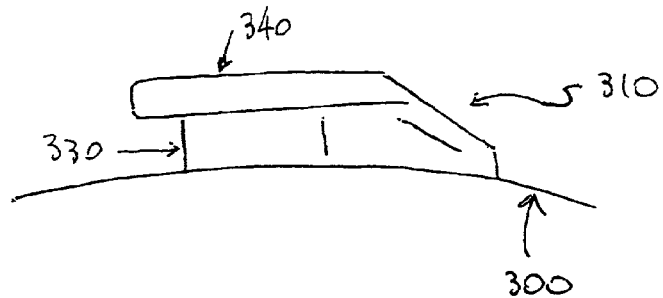
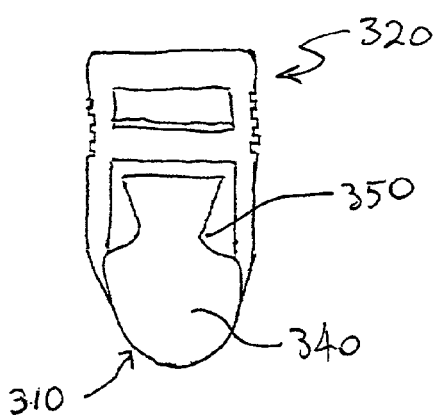
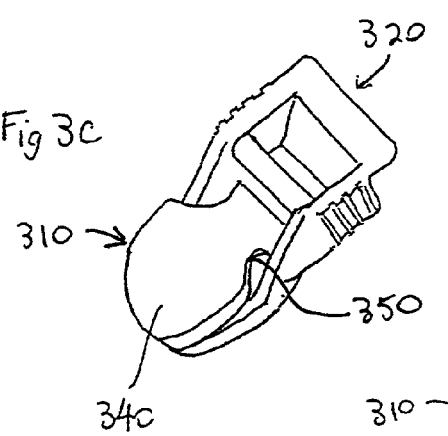
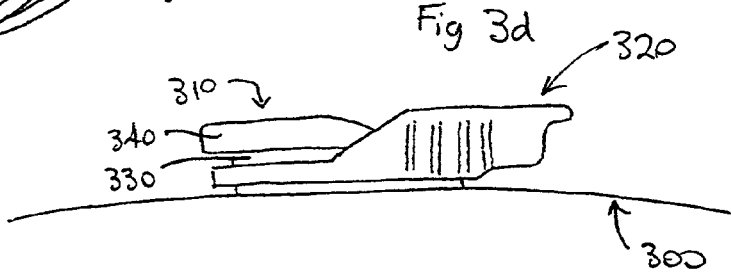

MASK AND HEADGEAR CONNECTOR

CROSS REFERENCE TO RELATED APPLICATIONS

This application is a continuation of U.S. application Ser. No. 09/504,220, filed Feb. 15, 2000, now U.S. Pat. No. 6,374,826, which is a Continuation-In-Part of U.S. Design Application No. 29/115,618, filed Dec. 16, 1999, now Design Pat. No. 443,355, the specification and drawings of which are incorporated herein by reference.

FIELD OF THE INVENTION

The invention relates to a connector for use with a mask and headgear suitable for the delivery of breathable gases to a patient for the treatment of sleep disordered breathing (SDB).

BACKGROUND OF THE INVENTION

Respiratory masks used in the treatment of SDB may comprise either a nasal mask, designed to fit over a patient's nose, or a full face mask designed to fit over the nose and mouth of the patient. Air or other breathable gas is supplied by a blower and passed along a flexible conduit to the mask.

The mask generally comprises a relatively rigid shell, termed a frame, which defines a rearwardly opening cavity covering the patient's nose and/or mouth and a soft portion, termed a cushion, which spaces the frame away from the face for comfortable contact.

The masks are typically held in place using headgear, the mask and headgear being joined using some form of connector.

One known example is the Mirage® Mask (ResMed Limited), shown in FIG. 1. In this case, the headgear 100 is constructed from fabric and includes a rear portion, which engages the region near the occiput of the patient, and four straps 110 which are secured to a forehead support 120 (2 straps) and nasal mask frame 130 (2 straps). The straps include hook and loop material, such as Velcro(TM) on one side. The mask frame and forehead supports include loops 140 through which a strap can pass. In order to secure the mask in place on a patient's head, the four straps are passed through the four corresponding loops and held in place at an appropriate length by the hook and loop material. The patient can adjust the length of the material in order to secure a good fit of the mask. In some cases, it can require considerable adjustment to find the optimal length of straps which is required. A difficulty with this connector is that if the patient removes the mask by loosening the straps, they will lose what may have been a good fit of the mask the next time it is being used. In this case they will need to repeat the adjustment step.

Another known manner of connecting the mask and headgear is shown in FIGS. 2a, 2b and 2c. In this headgear, a short strap length 200 is secured to one side of the mask, with a two-part, press-release connector 210, 220 attaching this to the strap 250 of the headgear. One disadvantage of the approach of using this arrangement is that the connector may be difficult to release because the connector is free to move relative to the mask frame. A further disadvantage of this arrangement is that the connector may be in contact with the patient's face which may lead to discomfort in use, particularly if they sleep on their side.

More detailed views of this prior art connector are shown in FIGS. 2b and 2c. Each part of the connector includes a bar 230, 240 behind which a respective one of the straps 200, 250 may be passed. The male portion 220 of the connector includes a resilient cantilever 260 which is captured behind a bar 270 on the female portion 210. The cantilever is depressed to engage and disengage the connector. A further disadvantage of this particular connector, best seen in FIG. 2b, is that it may be awkward to disengage the connector because of the close positioning of the bar 270 to the cantilever 260.

Another known mask and headgear connector is shown in FIG. 3a to FIG. 3d. This comprises a flexible part 310 positioned on the outer surface of a flexible mask frame 300 and a rigid part 320 formed generally as a D-ring with a loop to which the headgear strap is attached. The flexible part consists of a base 330 supporting an upper portion 340 (best illustrated in FIG. 3a) which overhangs the base portion 330 and has a narrow central region 350. In order to engage and disengage the connector, the flexible part 310 must be deformed whilst the D-ring of the rigid part is pushed over the upper portion 340 to engage below the overhanging ledge. This arrangement is awkward to engage and disengage and typically requires two hands.

Another known mask and headgear connector consists of hooks on the end of the headgear straps and corresponding holes in the mask frame. To engage the mask and headgear connector, the hook is passed through one of the corresponding holes on the headgear. This arrangement is also awkward to engage and disengage and typically requires two hands. Also, it is possible for the hooks to disengage during sleep as there is no locking means for the connection.

There is a need for a connector arrangement which is simple and quick to operate.

SUMMARY OF THE INVENTION

The invention provides, in one form, a respiratory mask and headgear combination comprising a respiratory mask having a rigid mask frame, adjustable headgear for securing said mask on a patient, said headgear including at least one attachment strap, said mask frame having rigidly secured thereto a rigid first connector, further comprising a second connector adapted for releasable mating with said first connector, said second connector having means for connection of said attachment strap of the headgear.

The invention further provides a respiratory mask and headgear combination adopted for single-handed disengagement, comprising a rigid mask frame, adjustable headgear for securing said mask on a patient, said headgear including at least one attachment strap, said mask frame having rigidly secured thereto a rigid first connector, further comprising a second connector connected to said strap of said headgear, said second connector being adapted for releasable mating with the first connector and having first and second gripping surfaces positioned for gripping of said second connector between a thumb and finger of a patient's hand and release means positioned for operation by another finger of the patient's hand.

BRIEF DESCRIPTION OF THE DRAWINGS

Further embodiments of the invention will now be described with reference to the accompanying drawings, in which:

FIG. 2b shows further detail of the prior art mask and headgear connector shown in FIG. 2a.

FIG. 3a shows a side view of another prior art mask and headgear connector where the two parts are not engaged.

FIG. 3b shows a top view of the prior art connector shown in FIG. 3a, where the two parts are engaged.

FIG. 3c shows a perspective view of the prior art connector shown in FIG. 3a, where the two parts are engaged.

FIG. 3d shows a side view of the prior art connector shown in FIG. 3a, where the two parts are engaged.

FIG. 6b shows a side view of FIG. 6a.

FIG. 6c shows a sectional view along A-A of FIG. 6a.

DETAILED DESCRIPTION OF THE INVENTION

Figure 1:
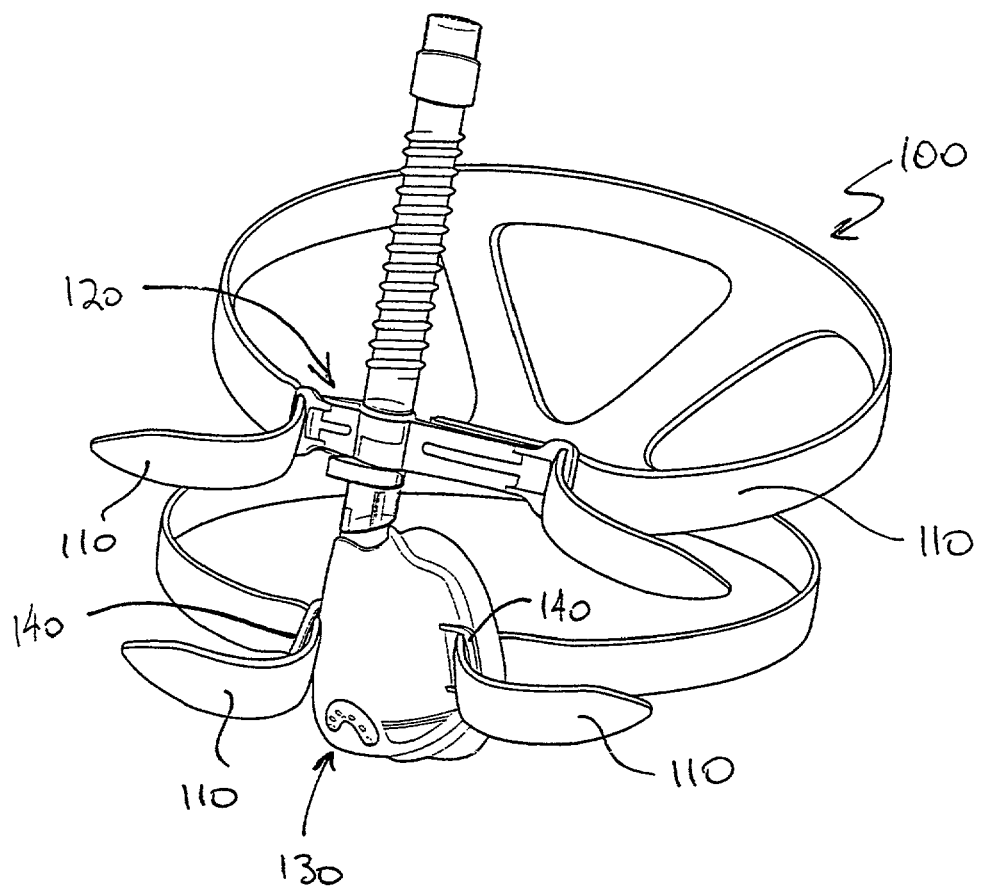
FIG. 1 shows the prior art Mirage® mask and headgear assembly.
Figure 2A:
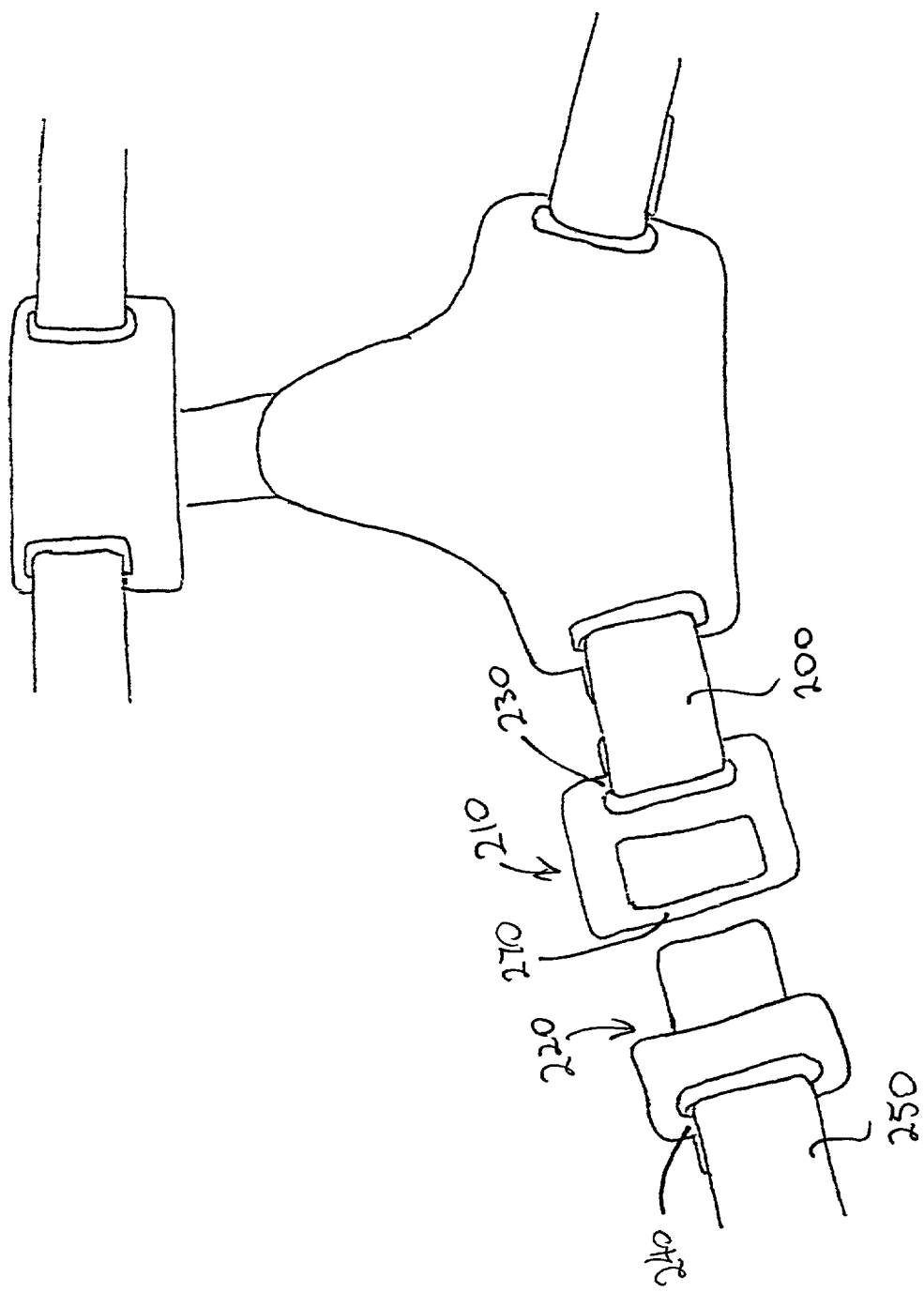
FIG. 2a shows a front view of a prior art mask and headgear assembly.
Figure 2B:
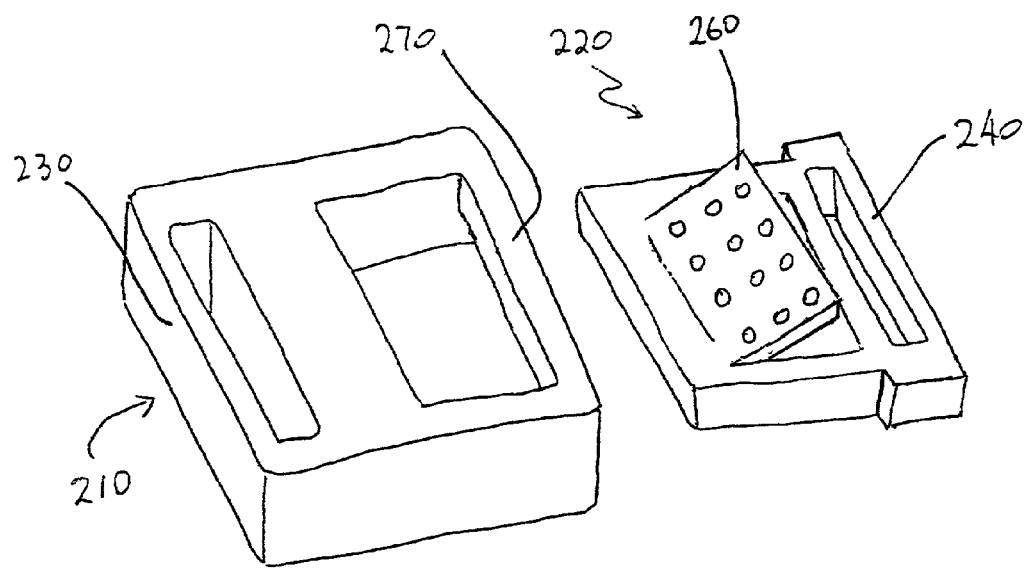
Figure 2C:
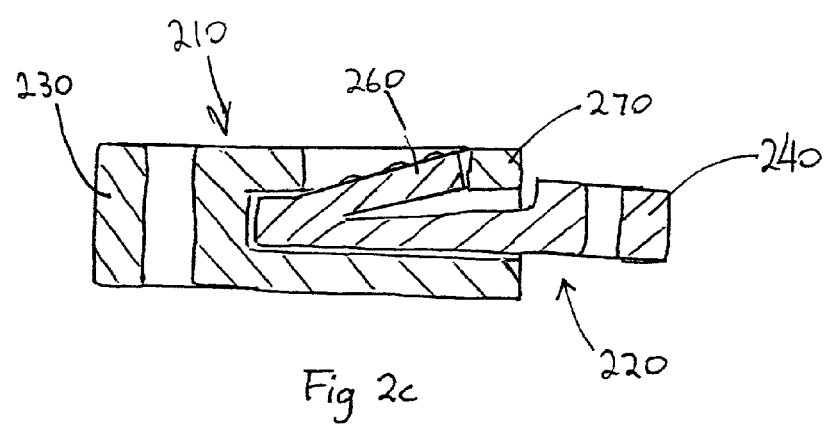
FIG. 2c shows a cross-sectional view of the prior art mask and headgear connector shown in FIG. 2b.
Figure 4:
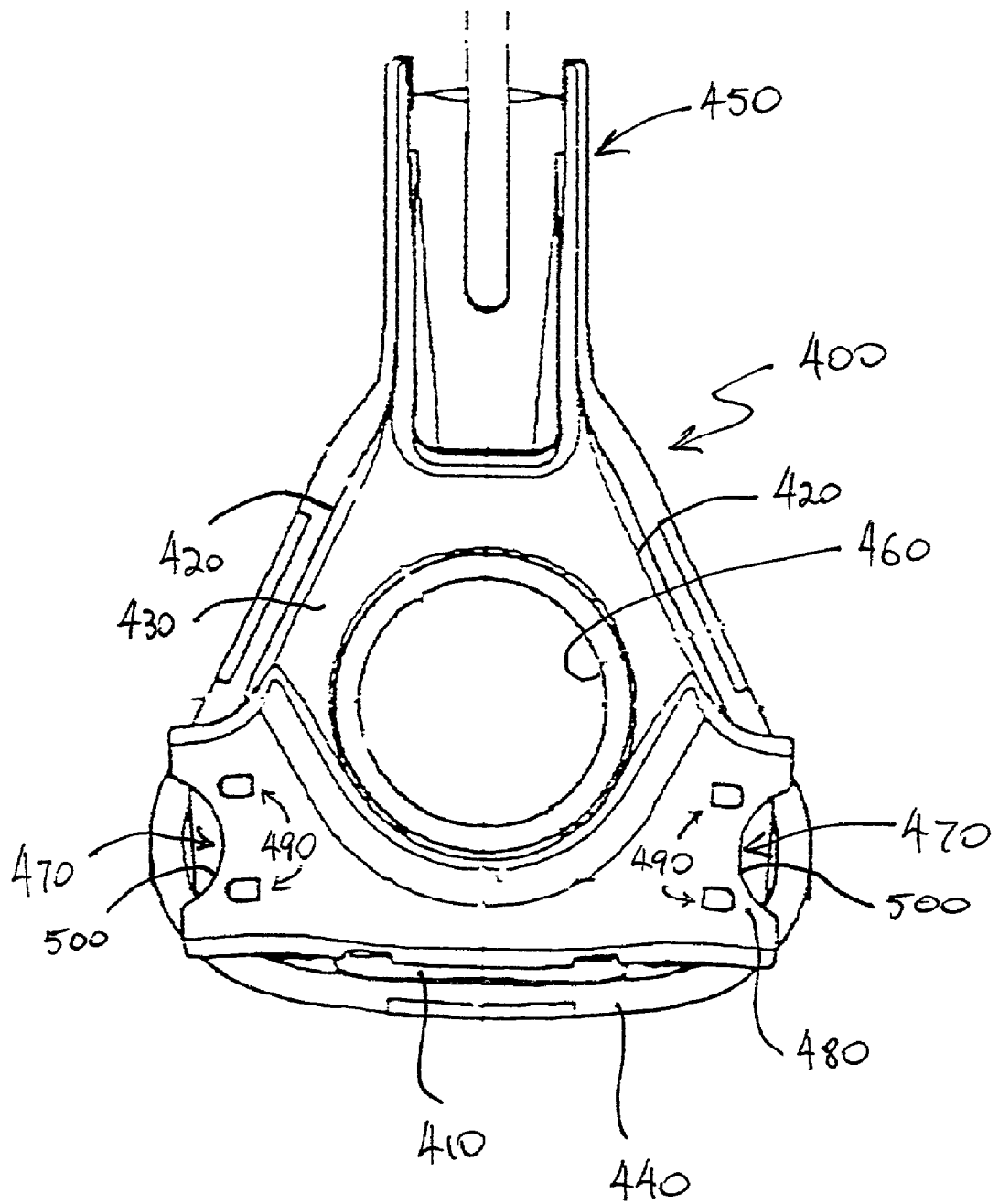
FIG. 4 shows a front view of a mask frame incorporating a female portion of the connector according to one embodiment of the invention.
Figure 5:
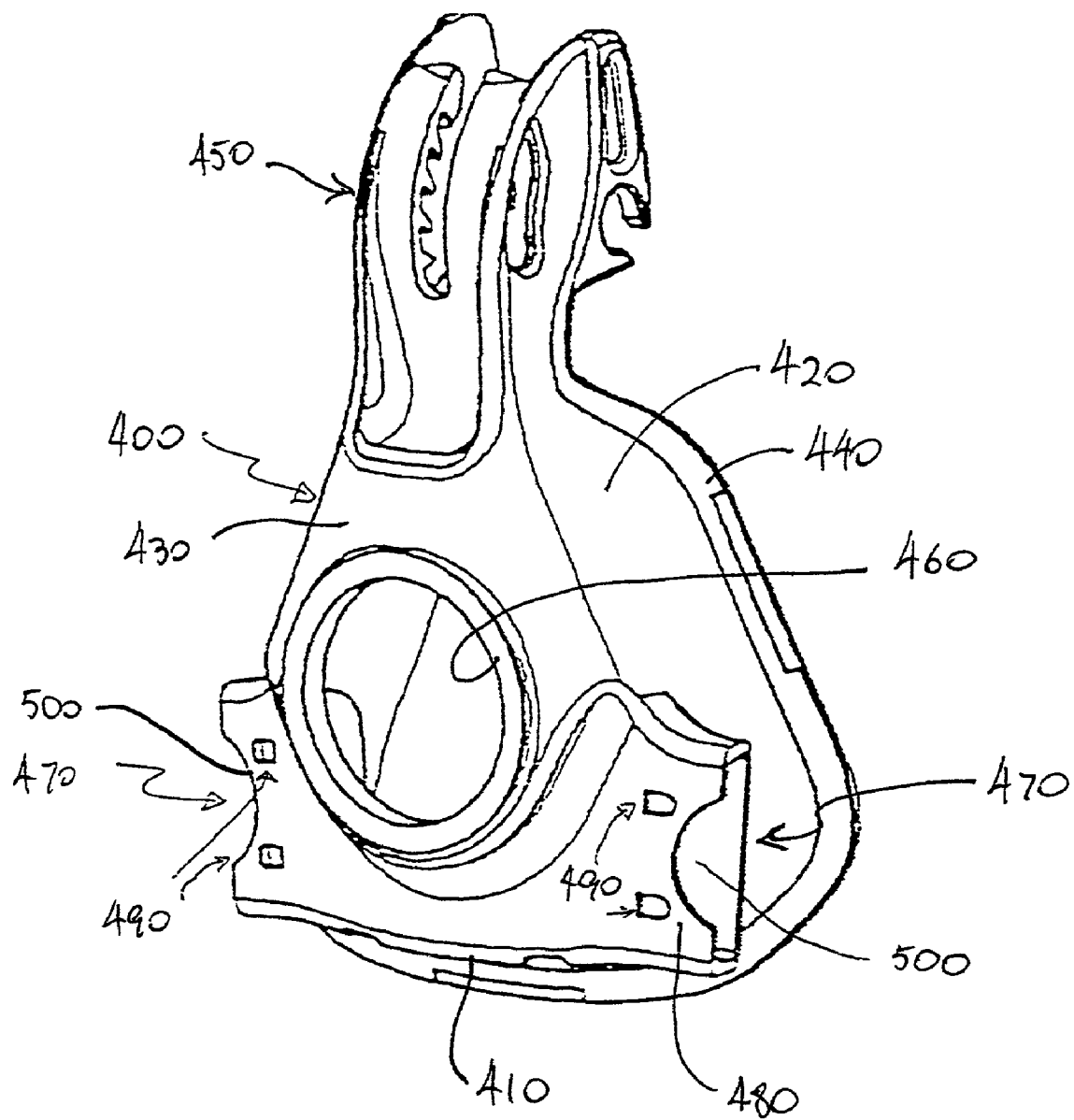
FIG. 5 shows a perspective view of the mask frame of FIG. 4.
Figure 6A:
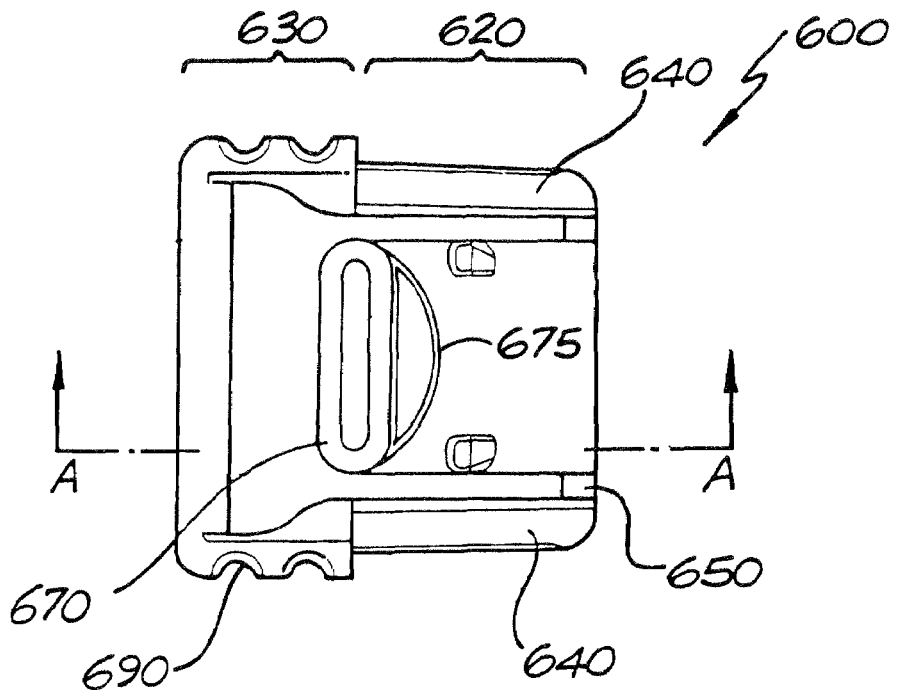
FIG. 6a shows a front view of a male portion of the connector adapted for use with the mask frame of FIGS. 4 and 5.
Figure 6B:
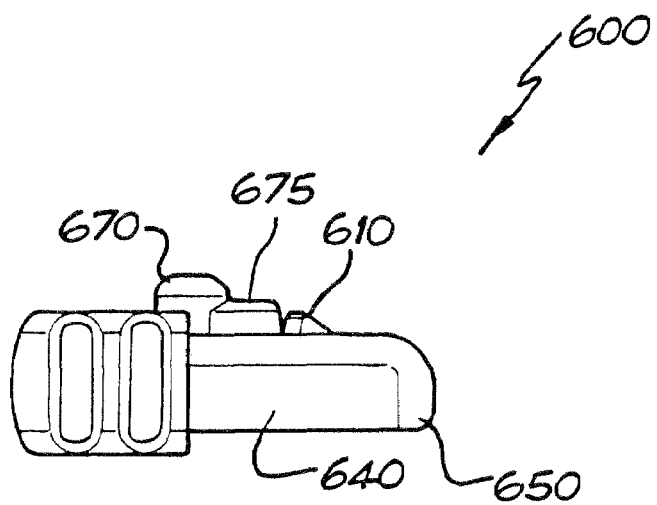
Figure 6C:
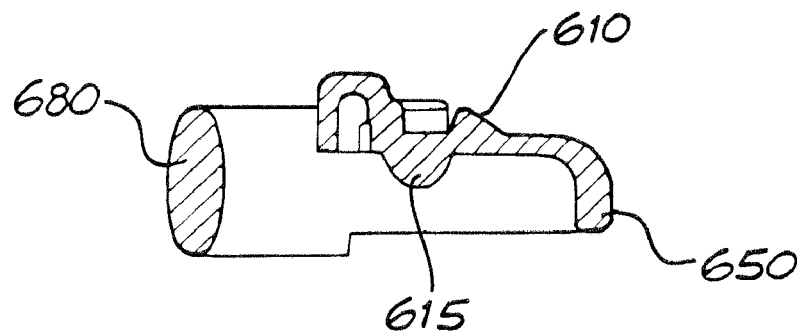
Figure 6D:
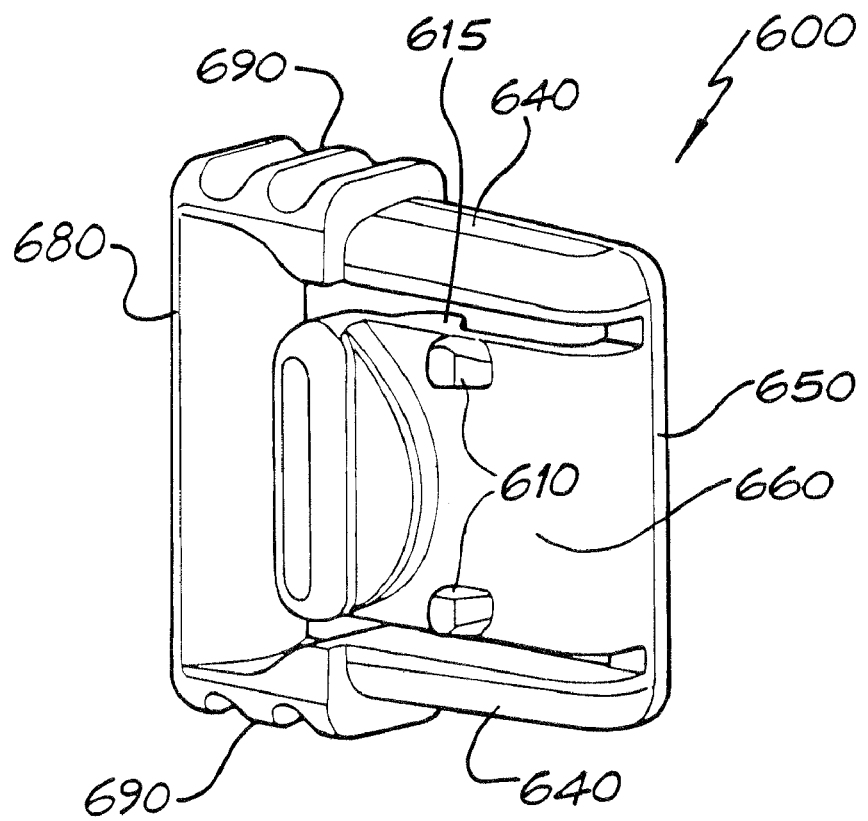
FIG. 6d shows a perspective view of FIG. 6d.

FIGS. 4 and 5 illustrate a mask frame 400 for a nasal mask, formed as a moulded shell of polycarbonate or similar rigid material, which acts as a body onto which the other components of the mask are attached.

The frame 400 is generally triangular in front view, having a base 410, a pair of inclined side walls 420 extending towards an apex and a front wall 430. The frame defines a mask cavity covering the patient's nose, and is open at its rear. A rim 440 at the rear edge of the base 410 and side walls 420 approximates the contours of the patient's face and is adapted for attachment of a soft mask cushion (not shown) to space the frame away from the patient's face for sealing and comfort. The apex of the frame has an extension 450 for attachment of a forehead support (not shown).

In the illustrated mask frame, a gas inlet aperture 460 is formed in the front wall 430, for connection of a gas supply conduit or similar, which may include an elbow connector (not shown) pivotably connected to the frame. In other forms of mask, the gas inlet aperture may be formed at the apex of the frame.

Integrally moulded into the lower corner regions of the rigid mask frame are a pair of female connector parts 470, for receiving the leading portions of the male connector parts 600, 700 illustrated in FIGS. 6a to 6d, or FIGS. 7a and 7b. These female connector parts open generally to the side of the mask, but are angled slightly downwards and rearwards (relative to the orientation of the mask frame) so that they hold the male connectors approximately parallel to that part of the patient's cheek region which the connectors overlie. The connectors are held clear of the patient's face by the rigid mask frame 400.

The female connectors 470 each define a recess which opens towards a side of the mask and which approximates a rounded-cornered rectangular in end view, adapted to provide a close fit with the corresponding male connectors 600,700 when engaged. These end shapes are preferably slightly asymmetric (keyed) so as to prevent upside-down insertion of the male connector.

A front wall 480 of the female connector has a pair of sockets 490 at least on its inner surface, for receiving respective lugs 610 of the male connector 600. The end of the front wall may also have a curved cut-out portion 500, as will be described below.

A corresponding male connector part 600 is illustrated in FIGS. 6a to 6d.

The male connector has a leading portion 620 which is received in the recess of the female connector 470, and a trailing portion 630 which remains outside the recess. The leading portion includes upper and lower side beams 640 connected by a crosspiece 650 at their leading ends, and a resiliently biased cantilever member 660 depending from the cross-piece 650 and extending back towards the trailing portion. The cantilever has on its front surface the lugs 610, and a ridge 670 at its trailing edge. The cantilever has on its back surface an arcuate projection 615 at a position between the lugs 610 and the ridge 670.

The locating lugs 610 have a rounded wedge profile so as to allow reduce wear and provide smooth engagement. The wedge profile does allow insertion of the male connector 600 into the female connector 470 on the mask without depression of the cantilever, although in preferred operation the patient will depress the cantilever by pushing on ridge 670 for both engagement and disengagement. Once the male connector has been inserted sufficiently to snap the locating lugs 610 into engagement with corresponding sockets 490 of the female connector, disengagement can occur only by depression of the cantilever.

The trailing portion 630 of the male connector has a cross-bar 680 forming a loop through which the headgear strap can be passed and adjusted for proper fit. Upper and lower sides 690 of the trailing portion have grooves or other formations to make it more easily gripped by the patient's fingers, while the distance between the leading side of the cross-bar 680 and the trailing edge and ridge 670 of the cantilever is preferably at least 5 mm to allow easy connection of the strap and provide sufficient space for a finger to push on the cantilever ridge, even when the strap is attached. The arcuate cut-out 500 in the female connector front wall is configured to contact an arcuate ridge 675 of the male connector 670 in the connected state and allows clearance for an end of the finger to overhang the ridge 670 when the ridge is being contacted by the pad of the finger.

Figure 7A:
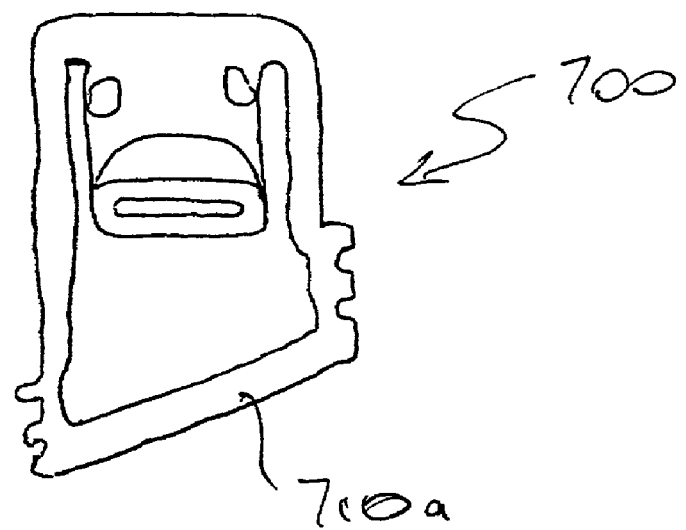
FIGS. 7a and 7b show an embodiment of the invention where the cross-bar on the male portions of the connectors have different angles.
Figure 7B:
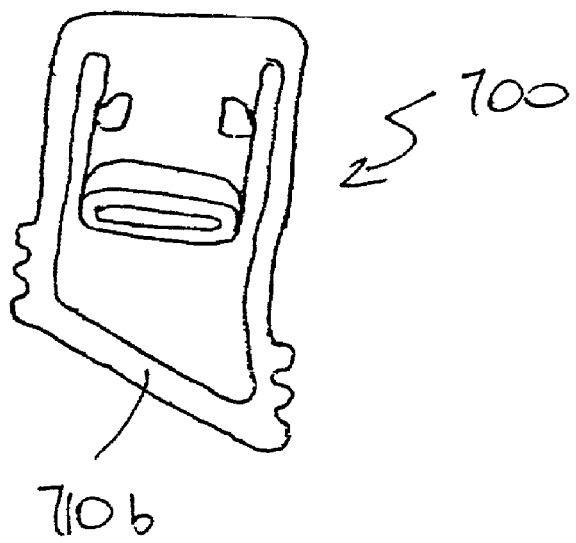

FIGS. 7a and 7b illustrate a male connector 700 which is a variation on that of FIGS. 6a to 6d, in that the cross bars 710a, 710b for attachment of the headgear strap are set at an angle.

The shape, dimensions and position of the connectors may be optimised for most convenient use. For example, the male connector may be approximately 20 mm wide, 25 mm long and 10 mm thick. The cantilever 660 is approximately 15 mm long. The locating lugs 610 are approximately 3 mm long, 2 mm wide and 1 mm high, and the ridge is approximately 14 mm wide and has a length of approximately 5 mm.

The female connectors 470 are oriented on the mask frame so that in use the straps of the headgear are aligned to be approximately parallel with the sides of the face with which they make contact. When viewed from the front of the mask (the view in FIG. 4), the tops of the left and right hand side male connector's cross-bars 680 are further apart than the bottoms of the cross-bars. When viewed from the top the mask, the connectors are aligned to be positioned on an arc of an ellipse. An advantage from this arrangement is that when straps are connected and tensioned, the line of force will be more evenly transferred from the mask to the frame.

Both portions of the connector are preferably constructed from polycarbonate, such as Makrolon 2458 polycarbonate from Bayer, or similar rigid plastics material. The female portions of the connectors are clear and desirably are integrally moulded with the mask frame which is formed of the same polycarbonate material, thus ensuring a permanent, rigid attachment of the female connector to the mask frame and minimising the number of separate parts. The male portions may be frosted or textured. An advantage from using a frosted or slightly textured surface is that the male portion may be easier to distinguish from the female portion by touch. This is an advantage in the dark, the typical time when the mask is being used by a patient.

The configuration thus allows single-hand operation of the connector using, for example, thumb and index finger to grip the grooved sides 690 of the male connector and the middle finger to depress the cantilever. The connectors may be located on both the left and right hand side of the mask. In this way persons may use which ever side is most convenient to them. Alternatively the frame may be formed with only one connector, to reduce manufacturing costs.

In one unillustrated embodiment, the press release mechanism may be adapted to be operated by pressing the top and/or bottom sides of the male connector.

By rigidly forming one part of the connector onto the mask frame, the patient does not need to use both hands to disconnect the mask for removal. Thus, the arrangement facilitates quick and easy disconnection even though the connector will be out of patient's line of vision and the patient may be less than fully awake or in an anxious state.

A further advantage of using female portions 470 integrated with the mask frame is that they result in a reduced dead volume of the mask frame.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

The invention claimed is:

1. A respiratory mask assembly comprising:
 a headgear structure including at least one strap portion having an;
 a male connector portion attached to the end of the at least one strap portion, the male connector portion including a trailing portion that has a pair of spaced side portions and a cross bar extending transversely therebetween, the male connector portion also including a leading portion that has a pair of longitudinally extending side beams spaced slightly inwardly from the side portions, the leading portion including a cross piece extending between the side beams and defining a leading edge of the male connector portion, the leading portion of the male connector portion also including a cantilevered member extending from an intermediate portion of the cross piece toward the trailing portion of the male connector portion, the cantilevered member being movable between deflected and undeflected positions and being resiliently biased toward the undeflected position, the cantilevered member including a locking element extending outwardly therefrom, the locking element being positioned on the cantilevered member generally spaced from the cross piece, the leading portion of the male connector portion including a ridge structure adjacent the trailing portion and extending generally perpendicularly relative to the side beams;
 a mask frame; and
 a female connector portion secured to the mask frame and being configured to receive the male connector portion therein.

2. The respiratory mask assembly of claim 1, wherein the mask frame includes a front wall portion defining a forward end of the mask frame, the front wall portion having a circular gas inlet aperture configured to connect to a gas delivery conduit, the mask frame including a pair of inclined side wall portions and a base portion, each side wall portion and the base portion having a portion thereof connected to the front wall portion.

3. The respiratory mask assembly of claim 2, wherein the mask frame includes a rim at rear edges of the inclined side wall portions and the base portion, the rim defining a rearward end of the mask frame and being configured to allow a cushion to be attached thereto.

4. A respiratory mask assembly according to claim 2, wherein the female connector portion is secured to the front wall portion of the mask frame.

5. A respiratory mask assembly according to claim 1, wherein each side portion of the trailing portion comprises at least one groove.

6. A respiratory mask assembly according to claim 1, wherein the locking element comprises two lugs on opposite sides of the cantilevered member.

7. A respiratory mask assembly according to claim 6, wherein each lug has a wedge profile.

8. A respiratory mask assembly according to claim 1, wherein the ridge structure is formed on the cantilevered member.

9. A respiratory mask assembly according to claim 1, further comprising an arcuate ridge between the ridge structure and the locking element.

10. A respiratory mask assembly according to claim 1, wherein the pair of spaced side portions and the cross bar define an aperture configured to receive the end of the at least one strap portion.

11. A respiratory mask assembly according to claim 1, wherein the mask frame comprises an extension configured for attachment of a forehead support.

12. A respiratory mask assembly according to claim 1, wherein the female connector portion is secured to the mask frame to permit the male connector portion to be connected to and disconnected from the female connector portion in a single-hand operation.

13. A respiratory mask and headgear combination comprising a respiratory mask having a rigid mask frame, and a headgear for securing said mask on a patient, said headgear including at least one attachment strap, said mask frame having secured thereto a rigid first connector portion, further comprising a second connector portion adapted for releasable mating with said first connector portion, said second connector being connected to said attachment strap, wherein
 said first and second connector portions form a press-release connection between said mask frame and said strap;
 said first connector portion is a female connector secured to said mask frame; and
 said second connector portion is a corresponding male connector, and
 said male connector includes a resiliently biased cantilever member depending from a leading end portion of said male connector and being lockable with said female connector.

14. A respiratory mask assembly according to claim 13, wherein the mask frame includes a front wall portion defining a forward end of the mask frame, the front wall portion having a circular gas inlet aperture configured to connect to a gas delivery conduit, the mask frame including a pair of inclined side wall portions and a base portion, each side wall portion and the base portion having a portion thereof connected to the front wall portion.

15. A respiratory mask assembly according to claim 14, wherein the mask frame includes a rim at rear edges of the inclined side wall portions and the base portion, the rim defining a rearward end of the mask frame and being configured to allow a cushion to be attached thereto.

16. A respiratory mask assembly according to claim 14, wherein the female connector is secured to the front wall portion of the mask frame.

17. A respiratory mask assembly according to claim 13, wherein the cantilever member comprises a lug configured to engage a socket in the female connector.

18. A respiratory mask assembly according to claim 17, wherein the lug has a wedge profile.

19. A respiratory mask assembly according to claim 13, wherein the mask frame comprises an extension configured for attachment of a forehead support.

20. A respiratory mask assembly according to claim 13, wherein the female connector is secured to the mask frame to permit the male connector to be connected to and disconnected from the female connector portion in a single-hand operation.

21. A respiratory mask for use with a headgear having first connector portions thereon, each of the first connector portions having one of a resiliently biased locking element and a locking element receiving aperture, the respiratory mask comprising:
a mask frame including a front wall portion defining a forward end of the mask frame, the front wall portion having a circular gas inlet aperture configured to connect to a gas delivery conduit, the mask frame including a pair of inclined side wall portions and a base portion configured in a generally triangular arrangement so as to define an upper vertex portion provided by an intersection of the inclined side wall portions and a pair of laterally spaced lower vertex portions provided by intersections of respective inclined side wall portions and the base portion, each side wall portion and the base portion having a portion thereof connected to the front wall portion; an extension member protruding generally radially outwardly relative to the circular gas inlet from the upper vertex, the extension member being configured to be coupled to a forehead support; the extension member providing an arcuate front wall member having a slot formed therein being oriented parallel to the extension member;
the mask frame includes an annular rim extending generally outwardly from rear edges of the inclined side wall portions and the base portion, the rim defining a rearward end of the mask frame and being configured to allow a cushion to be attached thereto;
a pair of second connector portions formed in one piece with the mask frame at respective lower vertex portions thereof, the second connector portions being configured to releasably engage with the first connector portions; wherein
each of the second connector portions includes a generally oblong slot, the generally oblong slot being formed by a base wall member that is disposed between a respective side wall portion and the base portion of the mask frame and being generally parallel to the front wall portion, a pair of parallel spaced opposing wall members extending generally perpendicularly from the base wall member, and structure disposed between the pair of spaced opposing wall members and being spaced from and generally parallel to the base wall member, the structure includes the other of the resiliently biased locking element and locking element receiving aperture; the base and opposing wall members and the structure having inward end portions and outward end portions defining a direction that extends generally radially outwardly relative to the circular gas inlet aperture; outward end portions of the base wall member and the opposing wall structures defining a generally C-shaped laterally facing surface contained within a single plane.

22. A respiratory mask assembly comprising:
a headgear structure including at least one elongate strap, one end of the elongate strap being doubled over to form a loop;
a pair of first connector portions attached to the elongate strap, each of the first connector portions including a trailing portion that has a pair of spaced side portions and a cross bar extending transversely therebetween to define a strap receiving aperture configured to allow the strap to pass therethrough so that the crossbar is disposed within the loop of the strap, each of the first connector portions also including a leading portion that has a pair of longitudinally extending side beams spaced slightly inwardly from the side portions, leading edge portions of the side beams being inwardly tapered toward the leading edges thereof, each of the first connector portions having one of a resiliently biased locking element and a locking element receiving aperture;
a mask frame including a front wall portion defining a forward end of the mask frame, the front wall portion having a circular gas inlet aperture configured to connect to a gas delivery conduit, the mask frame including a pair of inclined side wall portions and a base portion configured in a generally triangular arrangement so as to define an upper vertex portion provided by an intersection of the inclined side wall portions and a pair of laterally spaced lower vertex portions provided by intersections of respective inclined side wall portions and the base portion, each side wall portion and the base portion having a portion thereof connected to the front wall portion; an extension member protruding generally radially outwardly relative to the circular gas inlet from the upper vertex, the extension member being configured to be coupled to a forehead support; the extension member providing an arcuate front wall member having a slot formed therein being oriented parallel to the extension member;
the mask frame includes an annular rim extending generally outwardly from rear edges of the inclined side wall portions and the base portion, the rim defining a rearward end of the mask frame and being configured to allow a cushion to be attached thereto;
a pair of second connector portions formed in one piece with the mask frame at respective lower vertex portions thereof, the second connector portions being configured to releasably engage with the first connector portions; wherein
each of the second connector portions includes a generally oblong slot, the generally oblong slot being formed by a base wall member that is disposed between a respective side wall portion and the base portion of the mask frame and being generally parallel to the front wall portion, a pair of parallel spaced opposing wall members extending generally perpendicularly from the base wall member, and structure disposed between the pair of spaced opposing wall members and being spaced from and generally parallel to the base wall member, the structure including the other of the resiliently biased locking element and the locking element receiving aperture; the base and opposing wall members and the structure having inward end portions and outward end portions defining a direction that extends generally radially outwardly relative to the circular gas inlet aperture; outward end portions of the base wall member and the opposing wall structures defining a generally C-shaped laterally facing surface contained Within a single plane;

wherein the side beams of each first connector portion are capable of being passed through the oblong slot of the respective second connector portion, such that the side beams are disposed substantially between the base wall member and the structure and are disposed substantially between and parallel to the pair of spaced opposing wall members, the crossbar being disposed proximate and generally parallel to the outward end portions of the base wall member;

the resiliently biased locking elements being movable between deflected and undeflected positions and being resiliently biased toward the undeflected position; and the locking element receiving apertures being configured to locking engage with the resiliently biased locking elements when in the undeflected position.

23. A headgear for a respiratory mask assembly, the headgear comprising:

at least one strap portion having an end;

a male connector portion attached to the end of the at least one strap portion, the male connector portion including a trailing portion that has a pair of spaced side portions and a cross bar extending transversely therebetween, the male connector portion also including a leading portion that has a pair of longitudinally extending side beams spaced slightly inwardly from the side portions, the leading portion including a cross piece extending between the side beams and defining a leading edge of the male connector portion, the leading portion of the male connector portion also including a cantilevered member extending from an intermediate portion of the cross piece toward the trailing portion of the male connector portion, the cantilevered member being movable between deflected and undeflected positions and being resiliently biased toward the undeflected position, the cantilevered member including a locking element extending outwardly therefrom, the locking element being positioned on the cantilevered member generally spaced from the cross piece, the leading portion of the male connector portion including a ridge structure adjacent the trailing portion and extending generally perpendicularly relative to the side beams.

24. A headgear according to claim 23, wherein each side portion of the trailing portion comprises at least one groove.

25. A headgear according to claim 23, wherein the locking element comprises two lugs on opposite sides of the cantilevered member.

26. A headgear according to claim 25, wherein each lug has a rounded wedge profile.

27. A headgear according to claim 23, wherein the ridge structure is formed on the cantilevered member.

28. A headgear according to claim 23, further comprising an arcuate ridge between the ridge structure and the locking element.

29. A headgear according to claim 28, wherein a height of the arcuate ridge is less than a height of the ridge portion and more than a height of the locking element.

30. A headgear according to claim 23, wherein the pair of spaced side portions and the cross bar define an aperture configured to receive the end of the at least one strap portion, the aperture having a first width adjacent the cross bar and a second width adjacent the cantilevered member, the first width being greater than the second width.

31. A headgear according to claim 23, wherein a distance between a leading side of the cross bar and a trailing edge of the cantilever member is at least 5 mm.

32. A headgear according to claim 23, wherein the ridge structure has a width of approximately 14 mm and a length of approximately 5 mm.

33. A headgear according to claim 23, further comprising an arcuate projection extending inwardly from the cantilevered member.

34. A headgear according to claim 33, wherein the arcuate projection is positioned between the locking element and the ridge structure.

35. A respiratory mask and headgear combination comprising a respiratory mask having a rigid mask frame, adjustable headgear for securing said mask on a patient, said headgear including at least one attachment strap adapted to extend in a predetermined direction when coupled with the frame, said mask frame having secured thereto a substantially rigid first connector, further comprising a second connector adapted for releasable mating with said first connector, said second connector being connected to said attachment strap of the headgear, wherein said first and second connectors form a press-release connection;

said first connector is a female connector having a receiving slot, said female connector being secured to and extending laterally away from said mask frame such that the slot remains generally aligned with the predetermined direction of the strap;

said second connector is a corresponding male connector; and said male connector includes a resiliently biased cantilever member depending from a leading end portion of said male connector and being lockable with said female connector upon insertion of said leading end portion into the receiving slot of the female connector.

36. A respiratory mask assembly according to claim 35, wherein the female connector is secured to the mask frame to permit the male connector portion to be connected to and disconnected from the female connector portion in a single-hand operation.

37. A respiratory mask assembly according to claim 35, wherein the mask frame includes a front wall portion defining a forward end of the mask frame, the front wall portion having a circular gas inlet aperture configured to connect to a gas delivery conduit, the mask frame including a pair of inclined side wall portions and a base portion, each side wall portion and the base portion having a portion thereof connected to the front wall portion.

38. A respiratory mask assembly according to claim 37, wherein the female connector is secured to the front wall portion of the mask frame.

39. A respiratory mask assembly according to claim 37, wherein the mask frame includes a rim at rear edges of the inclined side wall portions and the base portion, the rim defining a rearward end of the mask frame and being configured to allow a cushion to be attached thereto.

40. A respiratory mask assembly according to claim 35, wherein the mask frame comprises an extension configured for attachment of a forehead support.

41. A respiratory mask assembly according to claim 35, wherein the cantilever member comprises a lug configured to engage a socket in the female connector.

42. A respiratory mask assembly according to claim 41, wherein the lug has a wedge profile.

* * * * *

UNITED STATES PATENT AND TRADEMARK OFFICE
CERTIFICATE OF CORRECTION

PATENT NO. : 7,600,513 B2
APPLICATION NO. : 10/090173
DATED : October 13, 2009
INVENTOR(S) : Gunaratnam et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1543 days.

Signed and Sealed this

Fifth Day of October, 2010

David J. Kappos
*Director of the United States Patent and Trademark Office*